United States Patent [19]

Dudeck et al.

[11] 4,165,342

[45] Aug. 21, 1979

[54] PREPARATION OF 3-ALKYL-BUTEN-1-ALS

[75] Inventors: Christian Dudeck, Limburgerhof; Hans Diehm, Mannheim; Fritz Brunnmueller, Ludwigshafen; Bernd Meissner, Heidelberg; Werner Fliege, Otterstadt, all of Fed. Rep. of Germany

[73] Assignee: BASF Aktiengesellschaft, Fed. Rep. of Germany

[21] Appl. No.: 892,785

[22] Filed: Apr. 3, 1978

[30] Foreign Application Priority Data

Apr. 5, 1977 [DE] Fed. Rep. of Germany ....... 2715209

[51] Int. Cl.² .............................................. C07C 45/16
[52] U.S. Cl. .................................................. 260/603 C
[58] Field of Search ..................................... 260/603 C

[56] References Cited

U.S. PATENT DOCUMENTS

| 2,042,220 | 5/1936 | Groll et al. | 260/603 C |
| 2,682,560 | 6/1954 | Carter et al. | 260/603 C |
| 3,086,852 | 4/1963 | Finske et al. | 260/603 C |

FOREIGN PATENT DOCUMENTS

| 2020865 | 11/1971 | Fed. Rep. of Germany | 260/603 C |
| 2041976 | 3/1972 | Fed. Rep. of Germany | 260/603 C |
| 2517859 | 11/1976 | Fed. Rep. of Germany | 260/603 C |

*Primary Examiner*—Werren B. Lone
*Attorney, Agent, or Firm*—Keil & Witherspoon

[57] ABSTRACT

3-Alkyl-buten-1-als are prepared by oxidative dehydrogenation of 3-alkyl-buten-1-ols in the presence of a silver catalyst, of a particular total thickness, comprising 2 or more layers each of a particular weight and containing particles of a particular size. The products are starting materials for the manufacture of dyes, pesticides, drugs, plastics, naturally occurring materials and scents.

15 Claims, 1 Drawing Figure

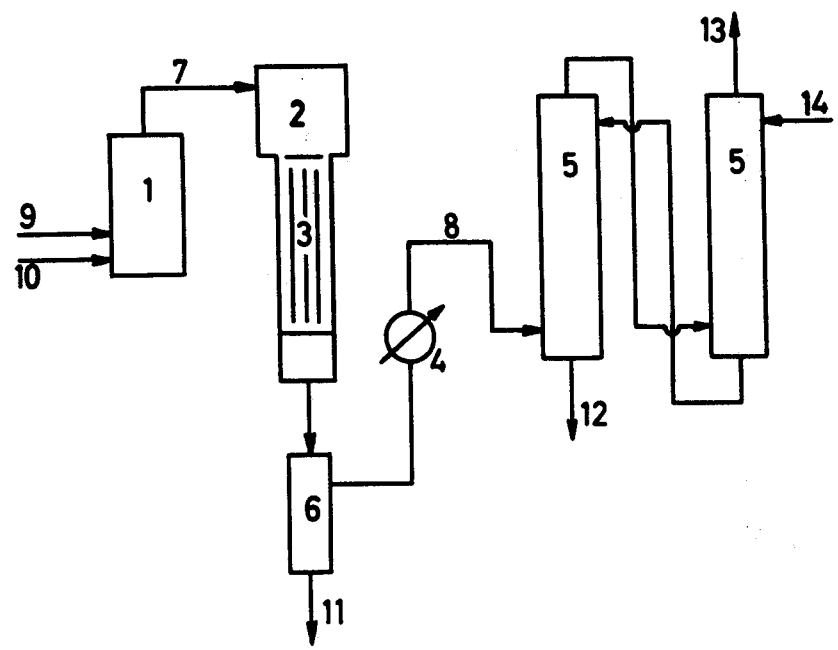

PREPARATION OF 3-ALKYL-BUTEN-1-ALS

The present invention relates to a novel process for the preparation of 3-alkyl-buten-1-als by oxidative dehydrogenation of 3-alkyl-buten-1-ols in the presence of a silver catalyst of a particular total thickness, which comprises 2 or more layers each of a particular weight and containing particles of a particular size.

U.S. Pat. No. 2,042,220 discloses the oxidation of 3-methyl-3-buten-1-ol with excess oxygen at from 360° to 550° C. in the presence of metal catalysts, e.g. copper and silver catalysts, to give 3-methyl-3-buten-1-al. The catalysts may be alloys, metal compounds or the elementary metal. Activated catalysts are preferred; activation operations mentioned are surface alloying of the metal and subsequent heating of the metal surface. The preparation of copper catalysts and silver catalysts, in the Examples, comprises reducing copper oxide wire at 300° C. in a hydrogen atmosphere, or alloying and heating silver wire mesh. As disclosed in German Laid-Open Application DOS No. 2,041,976, the reaction produces substantial amounts of isovaleraldehyde and isoprene. On admixture of oxygen, increasing amounts of dimethylacrylic acid are obtained, and the yield decreases substantially. German Laid-Open Application DOS No. 3,517,859 demonstrates that the end product obtained is not 3-butenal but in fact 3-methyl-2-buten-1-al.

German Laid-Open Application DOS No. 2,517,859 describes the dehydrogenation of unsaturated alcohols over a copper catalyst having a specific surface area of from 0.01 to 1.5 m$^2$/g, in the substantial absence of oxygen, at from 150° to 300° C. Where $\alpha,\beta$-unsaturated alcohols are used as starting materials, saturated aldehydes are formed as by-products; the selectivity for $\alpha,\beta$-unsaturated aldehydes is low (page 2, last paragraph). With respect to the prior art, to which the above publications belonged at the date of filing of DOS Nos. 2,517,859, 2,517,859 teaches that $\beta,\gamma$-unsaturated aldehydes can only be obtained with great difficulty from $\beta,\gamma$-unsaturated alcohols by the conventional processes, since high proportions of saturated aldehydes and $\alpha,\beta$-unsaturated aldehydes are formed (page 3, 1st paragraph). Such mixtures of the $\alpha,\beta$-unsaturated aldehydes and $\beta,\gamma$-unsaturated aldehydes must then for their part be separated from unconverted alcohol, for example by the process described in German Patent No. 2,243,810. In the process described in German Laid-Open Application DOS No. 2,517,859, the molar concentration of oxygen must be not more than 1/10 of the molar concentration of the alcohol starting material, and is preferably as low as possible.

German Patent No. 2,020,865 discloses the dehydrogenation of 3-methyl-3-buten-1-ol at from 150° to 600° C., in the presence of a mixed catalyst, for example of silver and/or copper and metal oxides, to give 3-methyl-2-buten-1-al. German Patent No. 2,243,810 draws attention to the fact that this method only gives good yields if the starting material is not completely converted. Furthermore, separating the end product from unconverted starting material by simple distillation is not possible, because of the small difference in boiling points. Preparation of the pure material is thus expensive and entails large losses in yield.

German Laid-Open Application DOS No. 2,041,976 discloses the conversion of 3-methyl-2-buten-1-ol to 3-methyl-2-buten-1-al at from 150° to 600° C. in the presence of dehydrogenation catalysts and additives, e.g. basic metal oxides, nitrogen compounds, phosphorus compounds or sulfur compounds. The Examples mention brass filings, copper oxide/zinc oxide/chromium oxide/aluminum oxide, copper/zinc oxide, silver/magnesium oxide and silver/zinc oxide as catalysts. German Laid-Open Application DOS No. 2,041,976 discloses (page 3) that oxide catalysts are in general superior to the pure metal catalysts and that substantial improvements in the dehydrogenation reaction are achieved if the actual dehydrogenation catalyst contains basic metal oxides. It further alleges that organic compounds possessing nucleophilic properties, inter alia sulfur compounds, suppress side-reactions (see bottom of page 4). It is a disadvantage that such compounds having nucleophilic properties, for example sulfur compounds are, in some cases, catalyst poisons. Additional disadvantages are that inert gases, for example from 20 to 50 percent by volume of steam, are admixed, and that the compounds with nucleophilic properties, added during the reaction, are contained in the reaction product.

We have found that 3-alkyl-buten-1-als of the formula

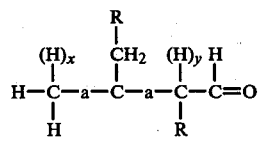

I where the individual radicals R may be identical or different and each is hydrogen or an aliphatic radical, of the two symbols a, one is a double bond and the other a single bond between the respective adjacent carbon atoms, and x and y are different and are each 0 if the adjacent symbol a is a double bond, or 1 if the adjacent symbol a is a single bond, are obtained advantageously by oxidative dehydrogenation of alkenols with oxygen in the presence of a metal catalyst if the reaction is carried out with 3-alkyl-buten-1-ols of the formula

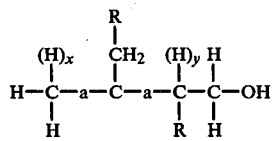

II where R, x, y and a have the above meanings, and with a catalyst, of total thickness from 5 to 35 mm, comprising 2 or more layers of silver crystals and/or copper crystals, one part of the layers containing from 10 to 50 percent by weight of the catalyst and having particles of size from 0.75 to 2.5 mm, and the remaining part of the layers containing from 50 to 90 percent by weight of the catalyst and having particles of size from 0.2 to 0.75 mm.

Further, it has been found that the above process may be carried out advantageously if a 3-alkyl-3-buten-1-ol of the formula

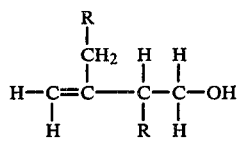

where R has the above meanings, is subjected to oxidative dehydrogenation in a first stage, and the resulting 3-alkyl-3-buten-1-al of the formula

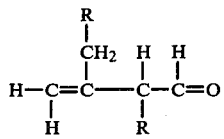

where R has the above meaning is isomerized catalytically, in a second stage, to give a 3-alkyl-2-buten-1-al of the formula

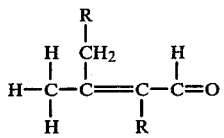

where R has the above meaning.

If 3-methyl-2-buten-1-ol or 3-methyl-3-buten-1-ol are used, the reaction can be represented by the following equations:

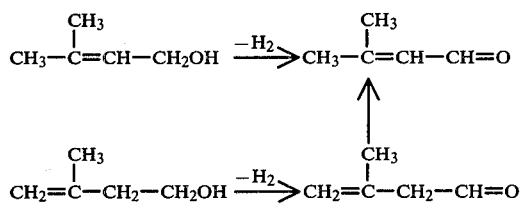

Compared to the prior art, the process of the invention surprisingly gives, by what is in part a simpler and more economical method, a better overall result in respect of yield, space-time yield, purity of the end product, and catalyst life. All these advantageous results are surprising in view of the prior art. It was to be expected from the disclosure of German Laid-Open Application DOS No. 2,020,865 that over a pure silver catalyst the dehydrogenation of β,γ-unsaturated alcohols would not produce any β,γ-unsaturated aldehydes but instead would produce α,β-unsaturated aldehydes. The use of metallic silver for the dehydrogenation of unsaturated alcohols also seems unsuitable according to the disclosures in German Laid-Open Application DOS No. 2,041,976. The results obtained according to the present invention are also surprising in view of German Laid-Open Application DOS No. 2,517,859, which discloses that the reaction must be carried out in the substantial absence of oxygen and at a reaction temperature of from 150° to 300° C., with steam as the carrier gas; furthermore, the catalyst must be reactivated (loc. cit., page 7, third paragraph). Reactivation of the catalyst of the invention is not necessary even after more than 1,000 operating hours.

Preferred starting materials II and IIa and accordingly preferred end products I, Ia and Ib are those where the individual radicals R may be identical or different and each is hydrogen or alkyl of 1 to 5 carbon atoms, of the two symbols a one is a double bond and the other is a single bond between the respective adjacent carbon atoms, and x and y are different and each is 0 if the adjacent symbol a is a double bond, or 1 if the adjacent symbol a is a single bond. The above radicals may additionally be substituted by groups which are inert under the reaction conditions, e.g. alkyl or alkoxy each of 1 to 4 carbon atoms.

Examples of suitable starting materials II and IIa are 3-methyl-, 3-ethyl-, 3-propyl-, 3-isopropyl-, 3-butyl-, 3-sec.-butyl-, 3-isobutyl-, 3-tert.-butyl and 3-pentyl-3-buten-1-ol; 2-methyl-, 2-ethyl-, 2-propyl-, 2-isopropyl-, 2-butyl-, 2-isobutyl-, 2-sec.-butyl- and 2-tert.-butyl-3-methyl-3-buten-1-ol; homologous 3-buten-1-ols substituted in the 3-position by the above groups of at least 2 carbon atoms and in addition in the 2-position by the above groups; and correspondingly substituted 2-buten-1-ols. 3-Methyl-2-buten-1-ol and 3-methyl-3-buten-1-ol are preferred.

The use of an inert gas is not essential but on the other hand does not interfere with the reaction. If desired, the catalyst can be heated by means of hot inert gases, advantageously nitrogen or combustion gases which contain little soot and no catalyst poisons; such gases may be, for example, at from 600° to 800° C.

Either pure oxygen or gases containing free oxygen, especially air, may be used as oxidizing agents. The oxygen, as a rule in the form of air, and the starting material II are advantageously used in a molar ratio of from 0.3 to 0.7, especially from 0.4 to 0.6, mole of oxygen per mole of starting material II.

The total thickness of the catalyst is from 5 to 35, preferably from 15 to 25, mm. The catalyst particles, in the form of silver crystals and/or copper crystals, are present, depending on particle size, in an upper part or a lower part of the total layer of catalyst contained in the reactor, which is advantageously set up vertically. The starting mixture of vaporous starting material II and oxygen or air is in general passed downward through the reactor so that the upper layer or layers constitute the part of the catalyst which faces the starting mixture. In reactors of different construction, or in the event of the starting mixture being passed through the reactor in a different manner, the same general principle applies, i.e., all references in the description to the upper or lower part of the catalyst mean the corresponding part which, respectively, faces the starting mixture or faces the discharged reaction mixture, for example, in the case of a horizontal reactor, the front and rear part of the catalyst respectively. The lower part contains from 10 to 50, preferably from 25 to 35, percent by weight of all catalyst particles and the upper part from 50 to 90, preferably from 65 to 75, percent by weight of all catalyst particles. The particles in the lower part of the bed have a size of from 0.75 to 2.5 mm and those in the upper part a size of from 0.2 to 0.75 mm. Each part of the bed can itself consist of one or more layers, preferably of 1, 2 or 3 layers. The use of a catalyst comprising from 3 to 7 layers, especially 3 or 4 layers, is preferred. Each of these layers differs from the others in the particle size of the silver crystals and/or copper crystals and in most cases also in respect of its proportion by weight of the total catalyst.

If the upper part of the bed comprises 2 layers, the upper layer preferably accounts for from 15 to 55 percent by weight and has particles of a size from 0.2 to 0.4 mm and the lower layer accordingly accounts for from 35 to 75 percent by weight and has particles of a size from 0.4 to 0.75 mm (percentages by weight of the total bed). If the upper part of the bed comprises 3 layers, the following proportions based on the total weight of catalyst are preferred, the size of the particles being given in parentheses: upper layer from 15 to 55 percent by weight (from 0.2 to 0.4 mm); middle layer from 15 to 25 percent by weight (from 0.4 to 0.6 mm); lower layer from 20 to 25 percent by weight (from 0.6 to 0.75 mm). Accordingly, the preferred figures for the lower part of the bed are:

(a) 1 layer: from 10 to 50% by weight (from 0.75 to 1 mm)
(b) 2 layers: upper layer from 8 to 48% by weight (from 0.75 to 1 mm)
  lower layer from 2 to 42% by weight (from 1.00 to 2.5 mm)
(c) 3 layers: upper layer from 4 to 30% by weight (from 0.75 to 1 mm)
  middle layer from 2 to 28% by weight (from 1 to 1.5 mm)
  lower layer from 2 to 28% by weight (from 1.5 to 2.5 mm).

The spreading of each individual layer is in most cases uniform, so that the thickness of the individual layer remains constant over its entire cross-section. In such cases, the thickness depends directly on the above proportions by weight of the total catalyst, and on the particular size of the particles. However, all or some or, advantageously, one layer can also be spread nonuniformly; for example, the greater part of the catalyst particles can be introduced at the center, at the sides or, advantageously at the edge of the layer, and accordingly only a relatively small residual amount is distributed over the remainder of the layer.

A particularly advantageous catalyst has the following composition:
Layer 1 (top layer): from 15 to 25% by weight of the catalyst, comprising particles of size from 0.2 to 0.4 mm
Layer 2: from 40 to 60% by weight of the catalyst, comprising particles of size from 0.4 to 0.75 mm
Layer 3: from 20 to 35% by weight of the catalyst, comprising particles of size from 0.75 to 1.0 mm
Layer 4 (bottom layer): from 2 to 20% by weight of the catalyst, comprising particles of size from 1.0 to 2.5 mm.

Preferably, the throughput is from 0.5 to 3 tonnes, especially from 1 to 2 tonnes, of vaporous starting material II per m$^2$ of catalyst bed cross-section per hour. For industrial-scale operation, the catalyst bed diameter is preferably at least 0.05 meter and advantageously from 0.1 to 3 meters. The use of silver crystals alone, or of mixtures of silver and copper, is preferred. The residence time for the reaction is advantageously from 0.001 to 1 minute, preferably from 0.01 to 0.6 minute in the case of the preparation of 3-alkyl-2-buten-1-als I or Ib and from 0.01 to 0.5 minute in the case of the preparation of 3-alkyl-3-buten-1-als I or Ia. The residence time is based on, and calculated for, the reaction zone without catalyst packing. For example, the reaction space of an empty reaction tube can serve as the basis of calculation.

The reaction is advantageously carried out at from 320° to 650° C., preferably at from 400° to 600° C., especially from 450° to 550° C., under atmospheric or superatmospheric pressure, batchwise or, preferably, continuously. The reaction can be carried out in the absence or presence of added solvents; water is a suitable solvent, advantageously in an amount of from 5 to 40, especially from 10 to 20, percent by weight based on starting material II. Furthermore, by-products from the preparation of the starting materials II may still be present in the latter, for example formaldehyde, 3-methyl-3-buten-1-yl formate, 4,4-dimethyl-1,3-dioxane, 3-methyl-butane-1,3-diol or 4-methyl-3,6-dihydro-2H-pyran, or a proportion of end product I, for example up to 10 percent by weight, based on starting material II.

The oxidation can be carried out as follows: the starting material II, with or without water, is introduced into a vaporizer, e.g. a falling film, and vaporized therein, advantageously at from 70° to 180° C. (if water is used, the starting material II and the water may be introduced separately or as a mixture). The gas mixture of vaporous starting material II and air, with or without inert gas and water vapor, is then passed through the catalyst, in the above amounts, at the reaction temperature. The process is in general carried out continuously, at pressures of from 0.5 to 3 bars, preferably from 0.8 to 1.8 bars. Advantageously, the silver catalyst is heated to 250°-500° C., preferably 380°-450° C., before starting the process. The start of the exothermic reaction is advantageously detected by adding air to the starting mixture and observing the temperature change in the catalyst. If the reaction starts, an immediate rise in temperature is observed; if the reaction does not start, the introduction of the cold air lowers the temperature. The temperature in the catalyst is advantageously measured by means of thermocouples. Once the reaction has started, the air is in general fed continuously into the vaporous starting mixture, which may be done by passing the air through the bottom of the vaporizer unit. It is advantageous to cool the reaction gases leaving the catalyst zone rapidly to, for example, 20°-160° C. This condenses the greater part of the end product I. The cooled gas mixture is then advantageously passed to an absorption tower in which the end product I is washed out of the gas mixture by means of a suitable solvent, e.g. dimethylformamide, dimethylsulfoxide, acetone, methanol or water or mixtures of these and/or by means of a condensate from previous reactions; the washing is advantageously effected in counter-current. The end product I is then isolated from the condensate and the absorbates in the conventional manner, for example by distillation.

In a preferred embodiment of the preparation of 3-alkyl-2-buten-1-als, the 3-alkyl-3-buten-1-al is prepared, in a first stage, by the oxidative dehydrogenation described above and the reaction mixture thus formed is isomerized catalytically (without first isolating the end product) in a second stage, advantageously in the presence of a strong acid or of a basic compound, advantageously at from 50° to 250° C. Suitable starting materials are the above starting materials IIa, or the compounds Ia, where R have the above general and preferred meanings. 3-Methyl-3-buten-1-ol and 3-methyl-3-buten-1-al are preferred. Advantageous reaction conditions for the isomerization are those described in German Patent Application P 27 15 208.5. The isomerization is advantageously carried out at from 72° to 225° C., preferably from 120° to 225° C., especially from 130° to 220° C., under atmospheric or superatmospheric pressure, batchwise or, preferably, continuously. In this embodiment, it is advantageous to use residence times of from 0.001 to 1, preferably from 0.01 to 0.6, minute in the first (oxidation) stage, and residence times of from 10 seconds to 300 minutes, preferably from 1 to 5 minutes, in the second (isomerization) stage. If desired, water or organic solvents which are inert under the reaction conditions, for example additional proportions of components such as 3-methyl-3-buten-1-al which are already contained in the reaction mixture, may be added to the reaction mixture from the first stage. Water may advantageously be present in the mixture for the second stage in a total amount of from 0 to 50, preferably from 2 to 25, percent by weight, based on starting material IIa, whilst the organic solvents may advantageously be present in the mixture in an amount of from 0 to 50, preferably from 2 to 40, percent by weight, based on starting material IIa. The isomerization may be carried out in a one-phase or two-phase mixture.

Suitable isomerization catalysts are strong acids or basic compounds. Strong acids, for the purposes of the invention, means organic or inorganic acids which are inert under the reaction conditions and have an acid exponent (pKa) of from −7 to +2.16; as regards the definition of the acid exponent or the pKa, reference may be made to Ullmanns Encyklopadie der technischen Chemie, volume 15, page 2. Examples of suitable acids are sulfuric acid, advantageously of from 10 to 98 percent strength by weight, phosphoric acid, advantageously of from 70 to 90 percent strength by weight, hydrochloric acid, advantageously of from 10 to 35 percent strength by weight, nitric acid, advantageously of from 60 to 98 percent strength by weight, perchloric acid, advantageously of from 10 to 70 percent strength by weight and formic acid, advantageously of from 10 to 98 percent strength by weight. It is also possible to use hydrogen chloride gas, boric acid, sulfonic acids, e.g. benzenesulfonic acid and p-toluenesulfonic acid, trichloroacetic acid, acidic ion exchangers, such as those described in Houben-Weyl, Methoden der Organischen Chemie, volume I/1, pages 528 et seq., preferably polystyrenesulfonic acid resins, phenolsulfonic acid resins and polyfluoroethylenesulfonic acids, or mixtures of the above. Preferred acids are concentrated hydrochloric acid and sulfuric acid or phosphoric acid, especially in the above concentrations. The acid is advantageously used in an amount of from 0.01 to 5, preferably from 0.1 to 1, percent by weight, based on the weight of starting material II.

In the case of a basic compound, the reaction is advantageously carried out with from 0.01 to 5, preferably from 0.05 to 1, percent by weight of basic compound, based on the weight of starting material II. Advantageous basic compounds are tertiary amines, alkaline earth metal compounds, ammonium compounds, tertiary phosphines and alkali metal compounds, as well as mixtures of the above. However, zinc compounds and primary or secondary amines can also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethylene-glycollate, sodium 1,2-propylene-glycollate, sodium 1,3-propylene-glycollate, sodium diethylene-glycollate, sodium triethylene-glycollate, sodium 1,2-dipropylene-glycollate, potassium methylate, potassium ethylate, potassium n-propylate, potassium isopropylate, potassium n-butylate, potassium isobutylate, potassium sec.-butylate, potassium tert.-butylate, potassium ethylene-glycollate, potassium 1,2-propylene-glycollate, potassium 1,3-propylene-glycollate, potassium diethylene-glycollate, potassium triethylene-glycollate, potassium 1,2-dipropylene-glycollate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N,N-dimethylaminoethanol, N,N-diethylaminoethanol, N,N-dipropylaminoethanol, triisopropanolamine, triethanolamine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine, triethylenediamine, dimethylamine, diethylamine, dipropylamine, diisopropylamine, dibutylamine, diisobutylamine, di-sec.-butylamine, di-tert.-butylamine, dibenzylamine, dicyclohexylamine, diamylamine, dihexylamine, N-methylaniline, N-ethylaniline, N-propylaniline, N-methyltoluidine, N-ethyltoluidine, N-propyltoluidine, N-methylaminoethanol, N-ethylaminoethanol, N-propylaminoethanol, pyrrolidone, piperidine, pyrrolidine, imidazole, pyrrole, N,N'-dimethylethylenediamine, N,N'-diethylethylenediamine, morpholine, hexamethyleneimine, difurfurylamine, N-methylcyclohexylamine, methylamine, ethylamine, propylamine, isopropylamine, butylamine, sec.-butylamine, tert.-butylamine, benzylamine, hexylamine, cyclohexylamine, amylamine, aniline, toluidine, aminoethanol, ethylenediamine, furfurylamine, ammonium acetate, ammonium propionate, tetrabutylammonium hydroxide, trimethylbenzylammonium hydroxide, triethyl-phosphine, tri-n-propyl-phosphine, triisopropyl-phosphine, tri-n-butyl-phosphine, triphenyl-phosphine, tri-(2-cyanoethyl)-phosphine, bis-(2-cyanoethyl)-phenyl-phosphine and bis-(ethyl)-phenyl-phosphine.

It is particularly advantageous to use phosphoric acid and, preferably, tertiary amines, especially the above tertiary amines.

The second stage of the reaction may be carried out as follows: the reaction mixture from the first stage, together with the catalyst, and with or without solvent, is kept for from 10 seconds to 300 minutes at the reaction temperature. The end product Ib is isolated from the reaction mixture in the conventional manner, as a rule by fractional distillation.

The 3-alkylbuten-1-als obtainable by the process of the invention are valuable starting materials for the preparation of dyes, pesticides, drugs, plastics, naturally occurring materials and scents, e.g. citral, vitamins, e.g. vitamins A and E, chrysanthemic acid and β-ionone. Regarding their use, reference may be made to German Patent No. 2,243,810, German Laid-Open Application DOS No. 3,041,976, German Patent No. 2,020,865 and U.S. Pat. No. 2,042,220. Hitherto, it has only been possible to prepare α,β-unsaturated aldehydes unsatisfactorily, in respect of yield, purity of the end product and simplicity and economy of operation, from α,β- or β,γ-unsaturated alcohols. The preparation of 3-alkyl-2-buten-1-ols, especially of the 3-methyl compound, is expensive; on the other hand, the corresponding 3-butene compounds are more easily accessible; for example, 3-methyl-3-buten-1-ol may be obtained from isobutene and formaldehyde. Accordingly, the oxidation of such 3-buten-1-ols to give 3-buten-1-als, and the subsequent isomerization of the reaction mixtures, provides a simple and economical method of preparing 2-buten-1-als, especially 3-methyl-2-buten-1-al, an intermediate for the synthesis of citral, in better yield and greater purity.

In the Examples which follow, parts are by weight.

EXAMPLE 1 (DRAWING 1)

An installation comprising a vaporizer (1), a vertical tubular reactor (2), a downstream cooler (3) and an absorption unit (5) is employed. The vaporizer is connected to the tubular reactor by the line (7). Up to the reactor, the line can be heated. The catalyst layer is located below the reactor top and is followed by the cooling zone (3). The condensate formed in the cooling zone and in the downstream cooling zone (4) collects in the receiver (6); the cooling zone is connected to the absorption unit (5) by the line (8). The absorption section comprises two double-walled absorption columns, in cascade arrangement, and with external cooling jackets. The two columns are packed with 10 mm glass Raschig rings. The off-gas escapes through line (13).

A catalyst of silver crystals (28 parts) of the following composition is introduced into the reactor (2):

|  | Proportion of the catalyst per cent by weight | Particle size mm |
| --- | --- | --- |
| Layer 1 (top) | 21.4 | from 0.2 to 0.4 |
| Layer 2 (middle) | 50.0 | from 0.4 to 0.75 |
| Layer 3 (middle) | 23.6 | from 0.75 to 1.0 |
| Layer 4 (bottom) | 5.0 | from 1.0 to 2.5 |

The diameter of the catalyst layer is 0.2 meter and the total thickness of the catalyst before starting the reaction is 20 mm.

The catalyst is heated to 460° C. by external application of heat. 80 parts of 3-methyl-2-buten-1-ol are introduced into the vaporizer through line (10) and are heated to 70° C. 110 parts of air per hour are then led into the vaporizer through line 9 and a glass frit, whereupon the temperature of the catalyst begins to rise. When the reaction starts—as is detectable by the rise in catalyst temperature—the amount of air is brought to 230 parts per hour in the course of 0.1 hour, and at the same time the amount of 3-methyl-2-buten-1-ol introduced through line (10), vaporizer (1) and line (7) and passed through the catalyst is brought to 349 parts per hour (corresponding to a throughput of 1.11 tonnes of 3-methyl-2-buten-1-ol per hour per square meter of catalyst bed cross-section). In addition, 236 parts of nitrogen are introduced, resulting in a pressure of 1.07 bars upstream from the catalyst, and a catalyst temperature of 500° C. The reaction mixture is then cooled to 25° in the cooling zone (3) of the reactor; 330 parts per hour of mixture condense and are collected in a receiver (6). The absorption (5) itself takes place in two stages in counter-current, in the form of a gas washing operation. 4,200 parts of dimethylformamide, at a temperature of −10° C. in the cascade (5), are fed in, as the absorbent liquid, through line (14). In the course of 5 hours, 1,745 parts of 3-methyl-2-buten-1-ol are passed over the catalyst. The reaction mixture obtained during these 5 hours in the condensation unit and the absorption unit, and collected through lines (11) and (12), is distilled. 302 parts of unconverted 3-methyl-2-buten-1-ol and 1,378 parts of 3-methyl-2-buten-1-al of boiling point 135° C. are obtained. The conversion is 82.7 percent and the yield of 3-methyl-2-buten-1-al is 97.8% of theory, based on 3-methyl-2-buten-1-ol converted.

EXAMPLE 2

Using the method described in Example 1, a mixture of 1,805 parts of 3-methyl-3-buten-1-ol and 319 parts of water is passed, with 910 parts of air but without addition of nitrogen, over the catalyst described in Example 1, in the course of 5 hours at 485° C. and 1.08 bars. After distillation, 349 parts of unconverted 3-methyl-3-buten-1-ol and 1,089 parts of 3-methyl-3-buten-1-al of boiling point 95° C. are obtained. The conversion is 80.7 percent and the yield of 3-methyl-3-buten-1-al is 76.6% of theory, based on 3-methyl-3-buten-1-ol converted.

EXAMPLE 3

Using the method described in Example 1, a mixture of 1,658 parts of 3-methyl-3-buten-1-ol and 290 parts of water is passed, with 830 parts of air, over 14 parts of a catalyst of the composition shown below, in the course of 5 hours at 500° C. and 1.09 bars:

|  |  | Metal | Proportion of catalyst (% by weight) | Particle size mm |
| --- | --- | --- | --- | --- |
| (top) | layer 1 | silver | 28.6 | 0.2–0.4 |
|  | layer 2 | crystals | 21.4 | 0.4–0.6 |
|  | layer 3 | copper | 21.4 | 0.6–0.75 |
| (bottom) | layer 4 | crystals | 28.6 | 0.75–1.0 |

(Layers 1–3 are the upper part of the bed and layer 4 the lower part of the bed).

After distillation, 264 parts of unconverted 3-methyl-3-buten-1-ol and 1,103 parts of 3-methyl-3-buten-1-al of boiling point 95.3° C. are obtained. The conversion is 84.1 percent and the yield of 3-methyl-3-buten-1-al is 81.0% of theory, based on 3-methyl-3-buten-1-ol converted.

EXAMPLE 4

A reaction mixture (2,054 parts, comprising 1,089 parts of 3-methyl-3-buten-1-al, 616 parts of water and 349 parts of 3-methyl-3-buten-1-ol), obtained from a reaction carried out as described in Example 2, is mixed with 4 parts of tri-n-butylamine and isomerized for 2 minutes at 200° C. and 25 bars (the pressure being obtained by means of nitrogen). After cooling and distilling the mixture, 1,067 parts of 3-methyl-2-buten-1-al (98% of theory) of boiling point 135° C. are obtained.

EXAMPLE 5

A reaction mixture (100 parts, comprising 97 parts of 3-methyl-3-buten-1-al, 2 parts of water and 1 part of 3-methyl-3-buten-1-ol), from a reaction carried out as described in Example 2 is mixed with 0.5 part of tri-n-butylamine and isomerized for 30 minutes at 75° C. After cooling and distilling the mixture, 93.5 parts of 3-methyl-2-buten-1-al are obtained in addition to 3 parts of unconverted 3-methyl-3-buten-1-al (97% conversion; yield virtually quantitative, based on 3-methyl-3-buten-1-al converted).

EXAMPLE 6

A reaction mixture from a reaction carried out as described in Example 2 (and containing 34.6 parts of 3-methyl-3-buten-1-al and 4.8 parts of water dissolved in 60.6 parts of 3-methylbutan-1-al) is mixed with 0.2 part of 75 percent strength by weight phosphoric acid and isomerized for 20 minutes at 140° C. and 10 bars (the pressure being obtained by means of nitrogen). After cooling and distilling the mixture, 33.2 parts of 3-methyl-2-buten-1-al (96% of theory) are obtained.

We claim:

1. A process for the preparation of 3-alkyl-buten-1-als of the formula

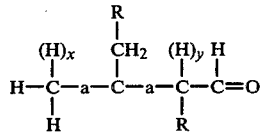   I where the individual radicals R may be identical or different and each is selected from the group consisting of hydrogen, alkyl of 1 to 5 carbon atoms and alkyl of 1 to 5 carbon atoms substituted by alkyl or alkoxy each of 1 to 4 carbon atoms, one of the two radicals a is a double bond and the other is a single bond between the respective adjacent carbon atoms, and x and y are different and are each 0 when the adjacent symbol a is a double bond and 1 when the adjacent symbol a is a single bond, which comprises reacting at from 320° to 650° C. a 3-alkyl-buten-1-ol of the formula

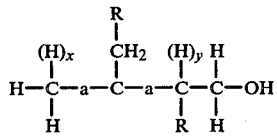   II where R, x, y and a have the above meanings, with oxygen in the presence of a catalyst of total thickness from 5 to 35 mm, said catalyst containing at least 2 layers of crystals selected from the group consisting of silver crystals, copper crystals and mixtures thereof, one part of the layers containing from 10 to 50 percent by weight of the catalyst and having particles of sizes from 0.75 to 2.5 mm, and the remaining part of the layers containing from 50 to 90 percent by weight of the catalyst and having particles of sizes from 0.2 to 0.75 mm.

2. A process as set forth in claim 1, wherein a 3-alkyl-3-buten-1-ol of the formula

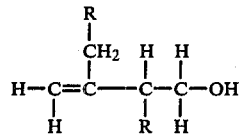   IIa where R has the above meaning, is subjected to oxidative dehydrogenation in a first stage, and the resulting 3-alkyl-3-buten-1-al of the formula

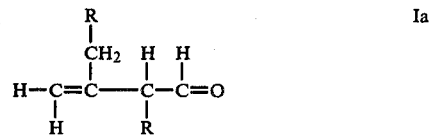   Ia where R has the above meaning is isomerized catalytically, in a second stage, to give a 3-alkyl-2-buten-1-al of the formula

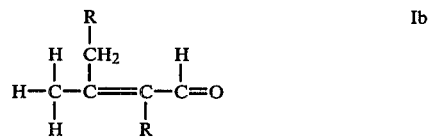   Ib where R has the above meaning.

3. A process as set forth in claim 1, wherein the oxidation is carried out with air using a molar ratio of from 0.3 to 0.7 mole of oxygen per mole of starting material II.

4. A process as set forth in claim 1, wherein the oxidation is carried out with from 25 to 35 percent by weight of all catalyst particles being present in the lower part of the catalyst and from 65 to 75 percent by weight of all catalyst particles being present in the upper part of the catalyst.

5. A process as set forth in claim 1, wherein the oxidation is carried out with a catalyst comprising from 3 to 7 layers.

6. A process as set forth in claim 1, wherein the oxidation is carried out with from 0.5 to 3 tonnes of vaporous starting material II per $m^2$ of catalyst bed cross-section per hour.

7. A process as set forth in claim 1, wherein the oxidation is carried out with residence times of from 0.001 to 1 minute.

8. A process as set forth in claim 1, wherein the oxidation is carried out at from 320° to 650° C.

9. A process as set forth in claim 1, wherein the oxidation is carried out at from 400° to 600° C.

10. A process as set forth in claim 1, wherein the oxidation is carried out at pressures of from 0.5 to 3 bars.

11. A process as set forth in claim 1, wherein the isomerization is carried out at from 72° to 225° C.

12. A process as set forth in claim 1, wherein the isomerization is carried out at from 120° to 225° C.

13. A process as set forth in claim 1, wherein the isomerization is carried out with residence times of from 10 seconds to 300 minutes.

14. A process as set forth in claim 1, wherein the isomerization is carried out with from 0.01 to 5 percent by weight of acid, based on the weight of starting material II.

15. A process as set forth in claim 1, wherein the isomerization is carried out with from 0.01 to 5 percent by weight of basic compound, based on the weight of starting material II.

* * * * *